US00PP24585P2

(12) United States Plant Patent
Kraan

(10) Patent No.: US PP24,585 P2
(45) Date of Patent: Jul. 1, 2014

(54) ***WEIGELA* PLANT NAMED 'BOKRASOPEA'**

(50) Latin Name: *Weigela hybrida*
Varietal Denomination: Bokrasopea

(75) Inventor: Kees Jan Kraan, Papenveer (NL)

(73) Assignee: Boot & Co., Baskoop (NL)

( * ) Notice: Subject to any disclaimer, the term of this patent is extended or adjusted under 35 U.S.C. 154(b) by 119 days.

(21) Appl. No.: 13/507,789

(22) Filed: Jul. 27, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

UPOV PLUTO Citation for 'Bokrasopea' Oct. 31, 2011.*

* cited by examiner

*Primary Examiner* — Wendy C Haas
(74) *Attorney, Agent, or Firm* — C. A. Whealy

(57) ABSTRACT

A new and distinct cultivar of *Weigela* plant named 'Bokrasopea', characterized by its relatively compact, upright and somewhat outwardly spreading plant habit; freely branching habit; dark green-colored leaves; freely and repeat-flowering habit; white-colored flowers that are tinged with red purple and with red purple-colored throats; and good garden performance.

2 Drawing Sheets

Botanical designation: *Weigela hybrida.*
Cultivar denomination: 'BOKRASOPEA'.

BACKGROUND OF THE INVENTION

The present invention relates to a new and distinct cultivar of *Weigela* plant, botanically known as *Weigela hybrida* and hereinafter referred to by the name 'Bokrasopea'.

The new *Weigela* plant is a product of a planned breeding program conducted by the Inventor in Boskoop, The Netherlands. The objective of the breeding program was to develop new compact and repeat-flowering *Weigela* plants with attractive leaf and flower colors.

The new *Weigela* plant originated from an open-pollination during the summer of 2000 of a proprietary selection of *Weigela hybrida* identified as code number 93028, not patented, as the female, or seed, parent with an unknown selection of *Weigela hybrida* as the male, or pollen, parent. The new *Weigela* plant was discovered and selected by the Inventor in June, 2007 as a single flowering plant from within the progeny of the stated open-pollination in a controlled environment in Boskoop, The Netherlands.

Asexual reproduction of the new *Weigela* plant by softwood cuttings in Boskoop, The Netherlands since the summer of 2007 has shown that the unique features of this new *Weigela* plant are stable and reproduced true to type in successive generations of asexual reproduction.

SUMMARY OF THE INVENTION

Plants of the new *Weigela* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Bokrasopea'.

These characteristics in combination distinguish 'Bokrasopea' as a new and distinct *Weigela* plant:

1. Relatively compact, upright and somewhat outwardly spreading plant habit.
2. Freely branching habit.
3. Dark green-colored leaves.
4. Freely and repeat-flowering habit.
5. White-colored flowers that are tinged with red purple and with red purple-colored throats.
6. Good garden performance.

In side-by-side comparisons conducted in Boskoop, The Netherlands, plants of the new *Weigela* differ primarily from plants of the female parent selection in the following characteristics:

1. Plants of the new *Weigela* are not as compact as plants of the female parent selection.
2. Plants of the new *Weigela* and the female parent selection differ in flower bud and flower color as plants of the female parent selection have pink-colored flower buds and flowers.

Plants of the new *Weigela* can be compared to plants of the *Weigela florida* 'Bristol Snowflake', not patented. In side-by-side comparisons in Boskoop, The Netherlands, plants of the new *Weigela* differed primarily from plants of 'Bristol Snowflake' in the following characteristics:

1. Plants of the new *Weigela* were more compact than plants of 'Bristol Snowflake'.
2. Plants of the new *Weigela* and 'Bristol Snowflake' differed in flower bud and flower color as plants of 'Bristol Snowflake' had white-colored flower buds and flowers.
3. Plants of the new *Weigela* had a repeat-flowering habit whereas plants of 'Bristol Snowflake' did not have a repeat-flowering habit.

Plants of the new *Weigela* can also be compared to plants of the *Weigela florida* 'Polka', not patented. In side-by-side comparisons in Boskoop, The Netherlands, plants of the new *Weigela* differed primarily from plants of 'Polka' in the following characteristics:

1. Plants of the new *Weigela* and 'Polka' differed in flower color as plants of 'Polka' had pink-colored flowers.
2. Plants of the new *Weigela* had a repeat-flowering habit whereas plants of 'Polka' did not have a repeat-flowering habit.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet comprises a side perspective view of a typical vegetative plant of 'Bokrasopea' grown in a container.

The photograph on the second sheet is a close-up view of a typical flowering plant of 'Bokrasopea'.

DETAILED BOTANICAL DESCRIPTION

The aforementioned photographs, following observations and measurements describe plants grown during the summer in one-gallon containers in an outdoor nursery in Grand Haven, Mich. and under commercial production practices. Plants were three years old when the photographs and description were taken. In the following description, color references are made to The Royal Horticultural Society Colour Chart, 2001 Edition, except where general terms of ordinary dictionary significance are used.

Botanical classification: *Weigela hybrida* 'Bokrasopea'.

Parentage:

*Female or seed, parent*.—Proprietary selection of *Weigela hybrida* identified as code number 93028, not patented.

*Male or pollen, parent*.—Unknown selection of *Weigela hybrida*, not patented.

Propagation:

*Type*.—By softwood cuttings.

*Time to initiate roots*.—About one month at temperatures of 20° C.

*Time to produce a rooted young plant*.—About six months at temperatures of 18° C.

*Root description*.—Medium in thickness; greyish brown in color.

*Rooting habit*.—Moderately freely branching; medium density.

Plant description:

*Plant and growth habit*.—Perennial shrub; relatively compact, upright and outwardly spreading plant habit; rounded crown; moderately vigorous to vigorous growth habit.

*Branching habit*.—Freely branching habit with numerous lateral branches developing per plant; dense and bushy plant form.

*Plant height*.—About 100 cm.

*Plant diameter*.—About 100 cm.

Lateral branch description:

*Length*.—About 6 cm to 8 cm.

*Diameter*.—About 4 mm.

*Internode length*.—About 8 cm.

*Angle*.—Erect to about 40° from vertical.

*Texture*.—Smooth, glabrous.

*Color, developing*.—Close to 144D.

*Color, fully developed*.—Close to 197D.

Foliage description:

*Arrangement*.—Opposite; simple.

*Length*.—About 5 cm.

*Width*.—About 1.5 cm to 2 cm.

*Shape*.—Elliptic.

*Apex*.—Acuminate.

*Base*.—Attenuate, tapering.

*Margin*.—Serrulate.

*Texture, upper surface*.—Smooth, glabrous.

*Texture, lower surface*.—Slightly pubescent.

*Venation pattern*.—Pinnate.

*Color*.—Developing and fully expanded leaves, upper surface: Close to 137A; venation, close to 144C. Developing and fully expanded leaves, lower surface: Close to 138A; venation, close to 144C.

*Petiole*.—Length: About 3 mm to 4 mm. Diameter: About 3 mm. Texture, upper and lower surfaces: Smooth, glabrous. Color, upper and lower surfaces: Close to 144B.

Flower description:

*Flower arrangement and habit*.—Salverform flowers arranged in terminal clusters of two to six flowers; flowers face mostly outwardly.

*Fragrance*.—None detected.

*Natural flowering season*.—Plants of the new *Weigela* flower from early to mid-June in Grand Haven, Mich.; repeat-flowering habit.

*Flower longevity*.—Flowers last about one week on the plant; flowers not persistent.

*Flower diameter*.—About 2.5 cm.

*Flower length* (*height*).—About 2.5 cm.

*Flower buds*.—Length: About 1.2 cm. Diameter: About 4 mm. Shape: Narrowly ovate. Color: Close to 155A tinged with close to 66C.

*Corolla*.—Arrangement: Salverform; four to five petals fused into a tube with separate petal lobes. Petal lobe length: About 1.5 cm. Petal lobe width: About 1 cm. Petal lobe shape: Oblong. Petal lobe apex: Obtuse. Petal lobe margin: Entire. Petal texture, upper and lower surfaces: Smooth, glabrous. Color: When opening and fully opened, upper surface: Lobe, close to 155A tinted with close to 66C; throat, close to 66A; color becoming closer to 66C with development. When opening and fully opened, lower surface: Lobe, close to 155A; tube, close to 155A.

*Sepals*.—Arrangement: Five in a single whorl, fused; campanulate calyx. Length: About 7 mm. Width: About 1.5 mm. Shape: Lanceolate. Apex: Acute. Margin: Entire. Sepal texture, upper and lower surfaces: Smooth; glabrous. Color, upper and lower surfaces: Close to 146C.

*Peduncles*.—Length: About 1 cm. Diameter: About 2 mm. Strength: Moderately strong; flexible. Texture: Smooth, glabrous. Color: Close to 144D.

*Reproductive organs*.—Stamens: Quantity and arrangement: Five per flower. Anther shape: Narrowly oblong. Anther length: About 5 mm. Anther color: Close to 155D. Pollen amount: Abundant. Pollen color: Close to 155D. Pistils: Quantity: One per flower. Pistil length: About 3.5 cm. Style length: About 3.3 cm. Style color: Close to 155D. Stigma color: Close to 155D. Ovary color: Close to 144D. Seeds and fruits: Seed and fruit development have not been observed on plants of the new *Weigela*.

Garden performance: Plants of the new *Weigela* have exhibited good tolerance to rain, wind and have been observed to tolerate temperatures from about −20° C. to about 33° C.

Pathogen & pest resistance: Plants of the new *Weigela* have not been observed to be resistant to pests and pathogens common to *Weigela* plants.

It is claimed:

1. A new and distinct *Weigela* plant named 'Bokrasopea' as illustrated and described.

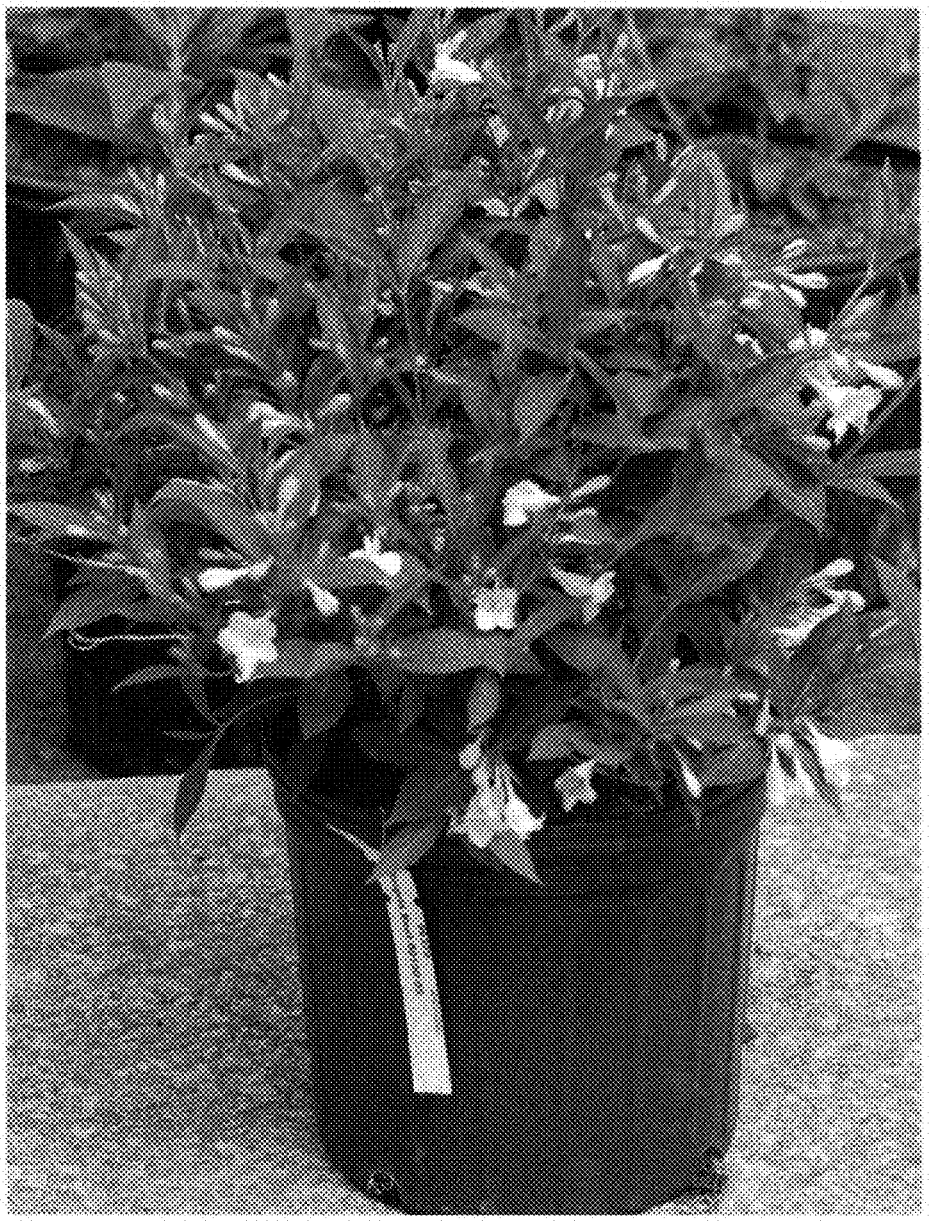

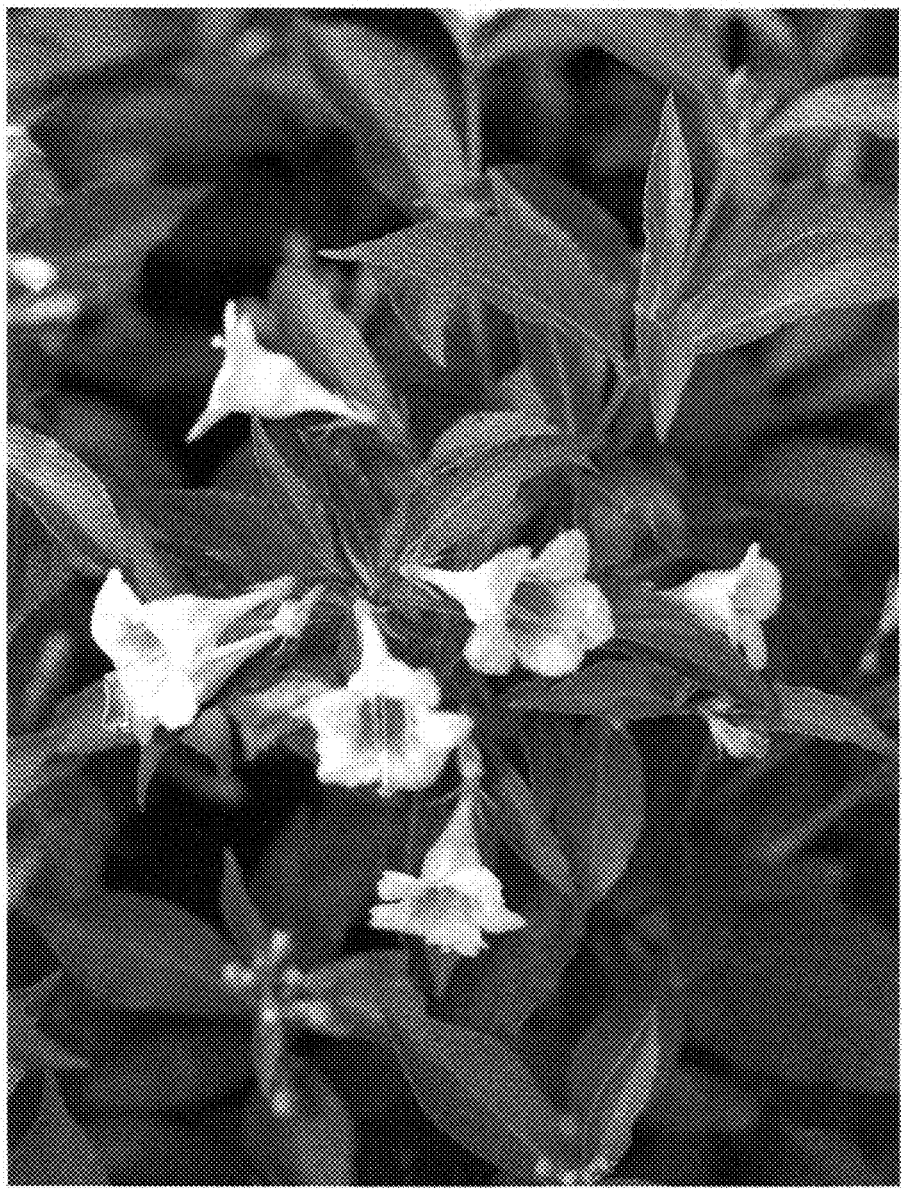

* * * * *